US00PP33212P3

(12) United States Plant Patent
Kahn et al.

(10) Patent No.: US PP33,212 P3
(45) Date of Patent: Jun. 29, 2021

(54) ***CANNABIS*PLANT NAMED 'V1'**

(50) Latin Name: *Cannabis sativa*
Varietal Denomination: V1

(71) Applicant: GenCann, LLC, Laytonville, CA (US)

(72) Inventors: Mikah Kahn, New York, NY (US); Brent Kaiser, Laytonville, CA (US); Blake Borges, Laytonville, CA (US); Michael Nazarian, Laytonville, CA (US); Justin Eric Delong, Laytonville, CA (US)

(73) Assignee: GenCann, LLC, Laytonville, CA (US)

( * ) Notice: Subject to any disclaimer, the term of this patent is extended or adjusted under 35 U.S.C. 154(b) by 0 days.

(21) Appl. No.: 16/602,084

(22) Filed: Aug. 5, 2019

(65) Prior Publication Data

US 2020/0329599 P1 Oct. 15, 2020

Related U.S. Application Data

(60) Provisional application No. 62/832,846, filed on Apr. 11, 2019.

(51) Int. Cl.

| | |
|---|---|
| ***A01H 5/02*** | (2018.01) |
| ***A01H 6/28*** | (2018.01) |
| *A61K 36/185* | (2006.01) |

(52) U.S. Cl.
USPC ..... Plt./258
CPC ..... *A01H 6/28* (2018.05); *A61K 36/185* (2013.01)

(58) Field of Classification Search
USPC ..... Plt./258, 263.1
CPC ... A01H 5/02; A01H 5/12; A01H 5/00; A01H 6/28; A61K 36/185
See application file for complete search history.

(56) References Cited

PUBLICATIONS

Hazelkamp et al. *Cannabis*: From Cultivar to Chemovar II—A Metabolomics Approach to *Cannabis* Classification, *Cannabis* and Cannabinoid Research, vol. 1.1, 2016 retrieved on Mar. 23, 2020, retrieved from the Internet at https://www.liebertpub.com/doi/pdfplus/10.1089/can.2016.0017, pp. 202-217. (Year: 2016).*

* cited by examiner

*Primary Examiner* — June Hwu
(74) *Attorney, Agent, or Firm* — Plant & Planet Law Firm

(57) ABSTRACT

The new *Cannabis* plant variety 'V1' is provided. 'V1' is intended for use as medicinal herb for sale in *Cannabis* dispensaries and for use in the manufacture of medicinal and recreational products. The variety can be distinguished by its outstanding features of increased production of tetrahydrocannabivarin (THCV) to a greater amount by percent weight than tetrahydrocannabinol (THC).

5 Drawing Sheets

Latin name of the genus and species:
Genus—*Cannabis.*
Species—*sativa.*
Variety denomination: The new *Cannabis* plant claimed is of the variety denominated 'V1'.

BACKGROUND OF THE INVENTION

The present invention relates to a new and distinct annual variety of *C. sativa*, which has been given the variety denomination of 'V1'. Its market class is that of a medicinal herb containing tetrahydrocannabinol (THC), and tetrahydrocannabivarin (THCV) 'V1' is intended for use as medicinal herb for sale in *Cannabis* dispensaries and for use in the manufacture of medicinal and recreational products.

The new *C. sativa* variety is a selection resulting from initial genetic selection of *C. sativa* varieties from Durban, South Africa and Malawi, Morocco to cultivate that had the potential for higher production of THCV. Plants were initially bred within greenhouses in Laytonville, Calif. before being acclimatized to outdoor conditions. After acclimatization, vegetative *C. sativa* plants were tested for THCV levels using chromatography. The highest THCV producing male and female plants were selected for breeding. The female parent F12 (not patented) of THC content 0.55% and THCV content 1.27% was cross bred to *C. sativa* male parent M31 (not patented) of THC content 6.14% and THCV content 1.24% to generate the F1 progeny. Cannabinoid production of the F1 progeny was measured beginning in 2016 and used to determine single plants to propagate F1 females having breeding record numbers Ma2, Ma3, Ma4, Ma5, Ma6, and Ma8 were open-pollinated with F1 males having breeding record numbers Ma1, Ma7, Ma9, and Ma10. F2 seeds were planted and F2 plants were selected for THCV production and vigor. The new variety was discovered and selected as a single plant from this cross of F1 parents, and was subsequently propagated clonally in Laytonville, Calif., U.S.A.

PROPAGATION

The selection was subsequently evaluated for 3 years in Laytonville, Calif., U.S.A. Individual plants were initially propagated within a greenhouse without supplemental lighting. Plants are transferred to outdoor growth once established.

Asexual reproduction of the new variety by stem cutting propagation since 2018 at Mendo Love Farms, Laytonville, Calif., U.S.A has demonstrated that the new variety reproduces true to type with all the characteristics, as herein described, firmly fixed and retained through successive generations of such asexual propagation.

HISTORICAL NOTE

Human cultivation history of *Cannabis* dates back 8000 years (Schultes, R. E. 1970. Random thoughts and queries on the botany of *Cannabis*. Pages 11-38 in: C R B Joyce, and S H Curry eds., THE BOTANY AND CHEMISTRY OF *CANNABIS*. J. & A. Churchill. London, England (1970)). Hemp cloth recovered in Europe dates back 6000 years (Small, F., Beckstead, H D., and Chan, A. 29(3) ECONOMIC BOTANY 219-232. (1975)). The written record of the pharmacologic properties of *Cannabis* goes back more than 4000 years (Ti, H. 2737BCE.Nei Jing Su Wen Huang Ti (Yellow Emporer's Classic on Internal Medicine; referred to without citation in Small, et al. (1975) Supra).

The taxonomy and nomenclature of the highly variable genus *Cannabis* (Emboden, W A., 29(3) ECONOMIC BOTANY 304-310. (1974)) (Small, E. and Cronquist, A. 25(4) TAXON 405-435 (1976)) (Small, E. and Cronquist, A. 26(1) TAXON 110 (1977)); (Hillig, K W and Mahlberg, P G, 91(6) American Journal of Botany 966-975 (2004)), remains in question. This is in spite of the fact that its formal scientific name, *Cannabis sativa* L., assigned by Carolus Linneaus (Linneaus, C, 2 SPECIES PLANTARIUM 1027 (1753), Salvius, Stockholm. Fascimile edition, 1957-1959. Ray Society, London, U.K.) is one of the oldest established names in botanical history and is still excepted to this day. Another species in the genus, *Cannabis indica* Lam. Was formally named somewhat later (de Lamarck, J B, 1(2) ENCYLOPEDIE METHODIQUE DE BOTANIQUE, 694-5, (1785)), but is still very old in botanical history.

Three other species names were proposed in the 1800s to distinguish plants with presumably different characteristics (*C. macrosperma* Stokes, *C. chinensis* Delile, *C. giganteam* Vilmorin), none of which are accepted today, although the epithet "indica" lives on as a subspecies of *C. sativa* (*C. sativa* ssp. *indica* Lam., Small and Cronquist 1976 Supra).

In the 20$^{th}$ century, two new names were added to the liturgy of proposed *Cannabis* species: *C. ruderalis* Janischevsky and a hybrid x '*C. interstita*' Sojak. (Small, E, Jui, P Y, and Lefkovitch, L P, 1(1) SYSTEMATIC BOTANY 67-84 (1976)); Small and Cronquist 1976, Supra). Further, numerous names have been proposed for horticultural variants of *Cannabis* but as of 1976, "very few of these have been validly published as formal taxa under the International Code of Botanical Nomenclature." (Small and Cronquist, 1976 Supra). Moreover, other recent work continues to focus on higher-order evolutionary relationships of the genus. *Cannabis* has been variously ascribed as belonging to the mulberry family (Moraceae) (Engler, H G A, Ulmaceae, Moraceae and Urticaceae, pages 59-118 (1889) in: A. Engler and K.Prantl eds., DIE NATURLICHEN PFLANZENFAMILIEN 3(1). W. Engelmann, Leipzeig, Germany; Judd, W S, Sanders, RW, and Donogue, M J, 5 HARVARD PAPERS IN BOTANY 5: 1-51 (1994)); nettle family (Urticaceae) (Berg, C C, Systematics and phylogeny of the Urticales, pages 193-220, in: P. R. Crane and S. Blackmore eds., EVOLUTION, SYSTEMATIC, AND FOSSIL HISTORY OF THE HAMAMELIDAE, VOL 2, HIGHER HAMAMELIDAE, Clarendon Press, Oxford, U.K. (1989); Humphries, C J and Blackmore, S. A review of the classification of the Moraceae, pages 267-277 In: Crane and Blackmore 1989 id.); and most recently in its own family with hops (*Humulus*), the Cannabaceae, or hemp family (Sytsma, K J m et al. 89(9) AMERICAN JOURNAL OF BOTANY 1531-1546 (2002)). While the work of Small and Cronquist 1976 Supra, seemed to effectively confine the genus to a single species with 2 subspecies (*C. sativa.s.*, *C. s. indica*), each with two varieties (*C.s.s* var *sativa, C.s.s.* var *spontanea; C.s.i.* var. *indica, C.s.i.* var. *Karfiristanica*) largely on the basis of chemotaxonomy and interfertility of all forms, more recent work (System, et al. 2002, Supra), proposes a two-species concept, resurrecting the binomial *C. indica* Lam. Since Systema, et al. 2002 provides no key for discriminating between the species, the dichotomous key of Small and Cronquist 1976 Supra, which accounts for all forms in nature, whether wild or domesticated, was used to classify the characteristics of the plants described herein.

The active ingredients in *Cannabis* are cannabinoids and include THC and THCV. Cannabinoids are of interest for their effects on the body through the endogenous cannabinoid system that is an integral part of the central nervous system.

SUMMARY OF THE INVENTION

The aim for the development of the new *C. sativa* variety, 'V1', was to produce a variety featuring increased THCV levels relative to THC levels. These phytocannabinoids in *Cannabis* are known for their ability to signal through the human endocannabinoid system. THC is found in the form of tetrahydrocannabolic acid (THCA) that is converted to THC during drying or under high heat. Similarly, THCV in live plants is in the form of tetrahydrocannabivarin carboxylic acid (THCVA). THC and THCV both bind to the cannabinoid receptors 1 ($CB_1$) and 2 ($CB_2$). Binding of $CB_1$ by its endogenous ligands, anandamide or 2-arachidonoylglycerol, stimulates food intake (Silvestri, C., Di Marzo, V. 17 Cell Metabolism 475-490 (2013)). THC acts as an agonist of $CB_1$ and stimulates appetite while THCV is a mild antagonist of $CB_1$ lessens sensations of hunger (Pertwee, R G. 153 British Journal of Pharmacology 199-215 (2008)). The ability of THCV to act as an antagonist of $CB_1$ has led to investigation of using THCV to treat metabolic syndrome and obesity (Riedel, G., et al., 156 British Journal of Pharmacology 1154-1166 (2009)). Selection of a variety producing increased amounts of THCV allows optimized isolation of THCV which may be used in treatment of metabolic syndrome.

Plants of the new variety differ from typical *C. sativa* plants in increased production of THCV compared to THC as determined by cannabinoid testing performed by an independent testing company. 'V1' demonstrates elevated THCVA levels 'V1' is a new variety with increased production of THCV compared to standard varieties of *C. sativa*. This enhanced production of THCV makes 'V1' a variety of interest for production of medicinal THCV.

TABLE 1

Exemplary Profiles of Key Cannabinoids.

| | Percent | Percent | Percent | Percent | Percent |
|---|---|---|---|---|---|
| d9-THC | 0.00 | 0.02 | 0.15 | 0.29 | 0.35 |
| THCA | 0.58 | 1.16 | 2.89 | 5.33 | 6.40 |
| Total THC* | 0.51 | 1.04 | 2.69 | 4.96 | 5.95 |

TABLE 1-continued

Exemplary Profiles of Key Cannabinoids.

| | Percent | Percent | Percent | Percent | Percent |
|---|---|---|---|---|---|
| THCV | 0.00 | 0.02 | 0.13 | 0.24 | 0.29 |
| THCVA | 1.00 | 1.71 | 3.56 | 5.56 | 6.67 |
| THCV + THCVA | 1.00 | 1.73 | 3.69 | 5.80 | 6.96 |
| CBG + CBGA | 0.00 | 0.12 | 0.27 | 0.54 | 0.64 |
| CBCA | 0.00 | 0.07 | 0.16 | 0.32 | 0.38 |
| Total Cannabinoid | 1.75 | 2.99 | 6.89 | 11.75 | 14.25 |
| THCV/THC (%) | 196 | 166 | 137 | 116 | 117 |
| THCV/Total Cannabinoid ( %) | 57 | 58 | 54 | 49 | 49 |

*Total THC = (THCA * 0.877) + THC (i.e. delta 9 THC) + delta 8 THC

BRIEF DESCRIPTION OF PICTURES

The accompanying photographs show the typical appearance of the new variety 'V1'. The colors are as nearly true as is reasonably possible in a color representation of this type. Colors in the photographs may differ slightly from the color values cited in the detailed botanical description which accurately describes the colors of the new plant.

FIG. 1 is a photograph of the new variety 'V1' at about age 12 weeks in its vegetative stage at a farm in Laytonville, Calif., U.S.A. in a 15-gallon pot. The photograph was taken in July 2018 and compares 'V1' with 'V2' (U.S. Provisional Pat. No. 62/832,859). 'V1' is on the left of 'V2'.

FIG. 2 is a photograph of the new variety 'V1' at about age 14 weeks in its vegetative stage at a farm in Laytonville, Calif., U.S.A. after pruning. The photograph was taken in July/August 2018 and compares 'V1', 'V2', and 'V3' (U.S. Provisional Pat. No. 62/832,863). 'V1' is in the center. 'V2' is on the left of 'V1' and 'V3' is on the right of 'V1'.

DETAILED BOTANICAL DESCRIPTION

Figure 1:
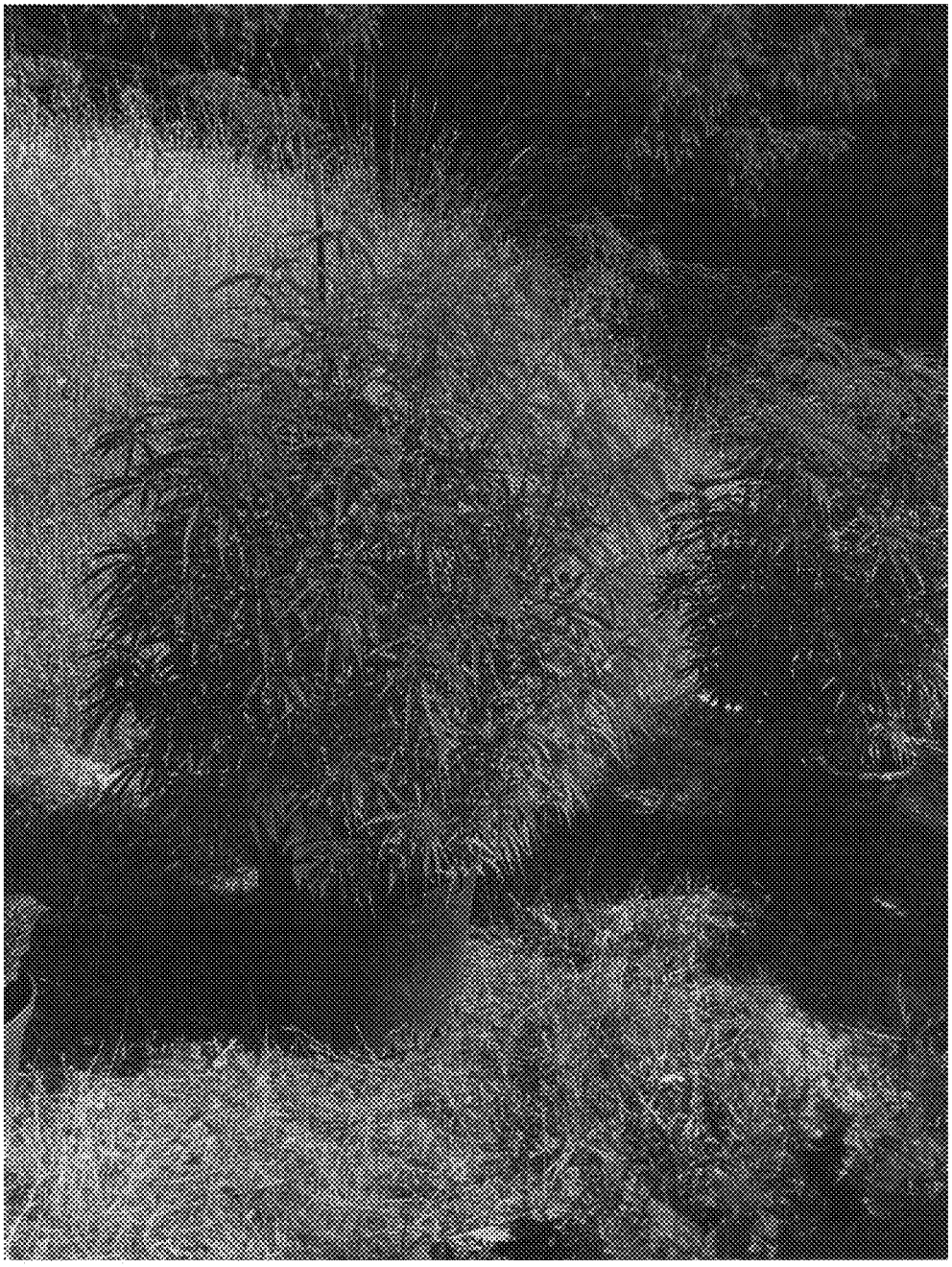
Figure 2:
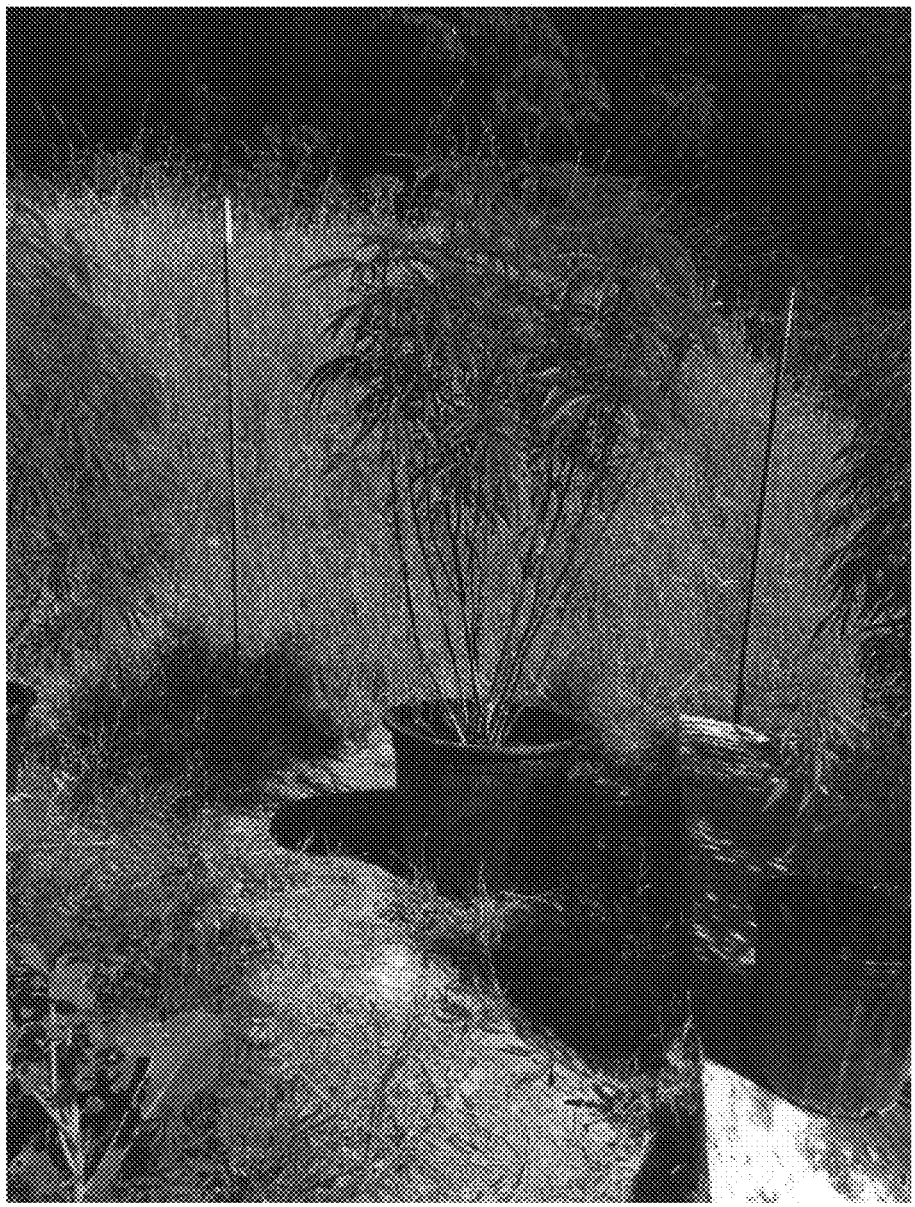
Figure 3:
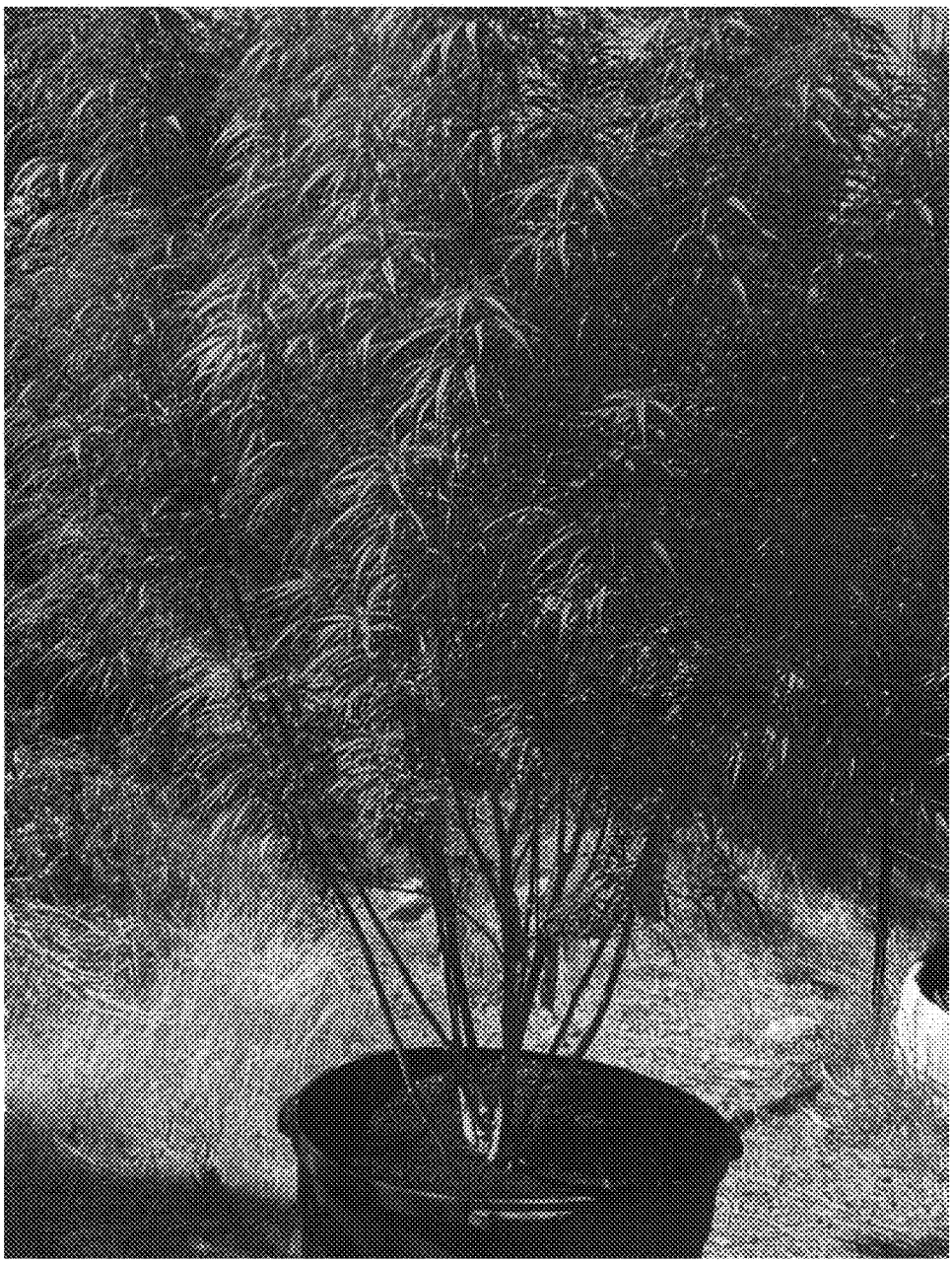
FIG. 3 is a photograph of the new variety 'V1' at about age 28-30 weeks in its vegetative stage at a farm in Laytonville, Calif., U.S.A. after pruning and in a 45-gallon pot.
Figure 4:
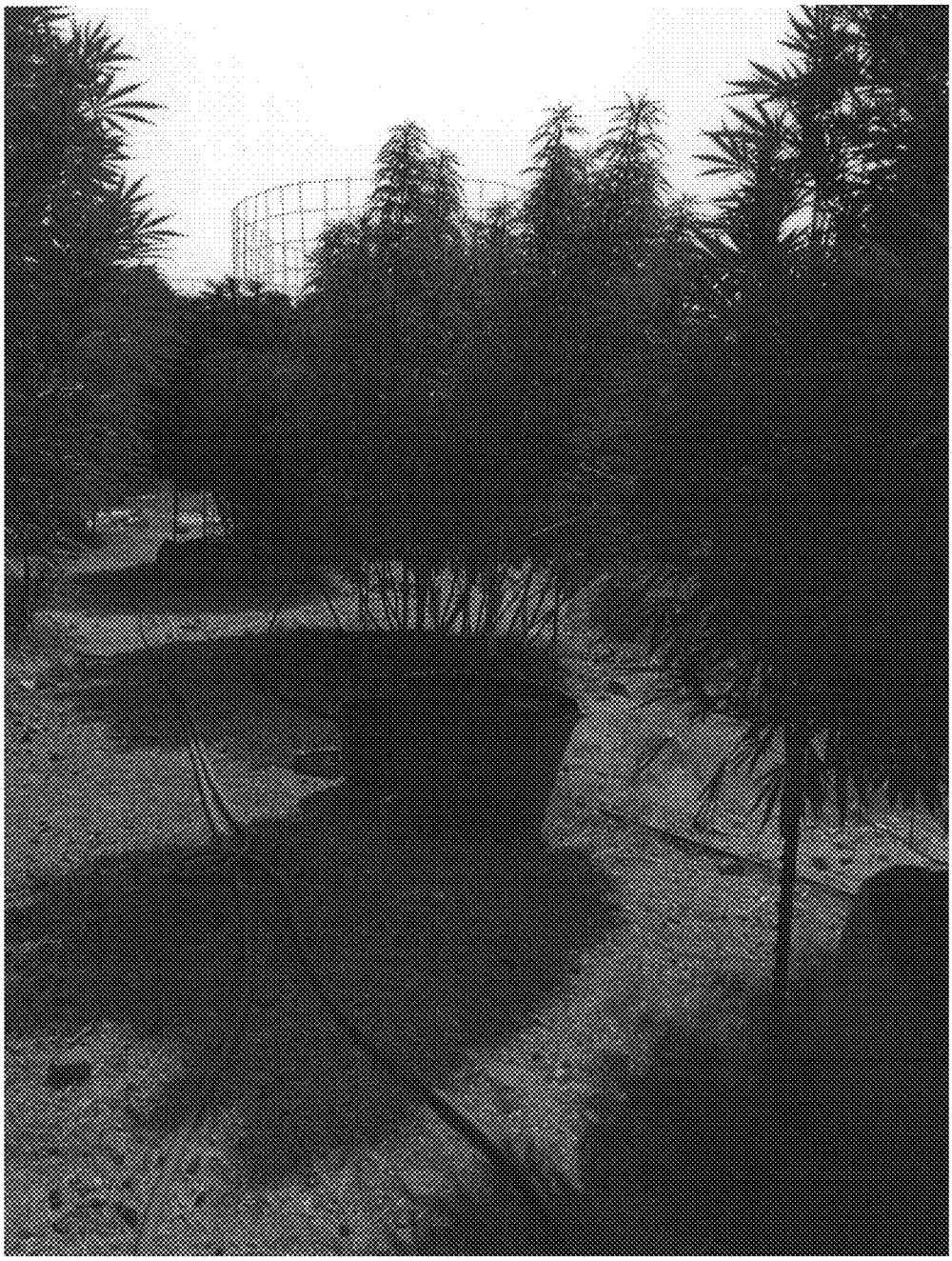
FIG. 4 is a photograph of the new variety 'V1' at about age 28 weeks in its vegetative stage at a farm in Laytonville, Calif., U.S.A. in a 45-gallon pot. The photograph was taken in October 2018.
Figure 5:
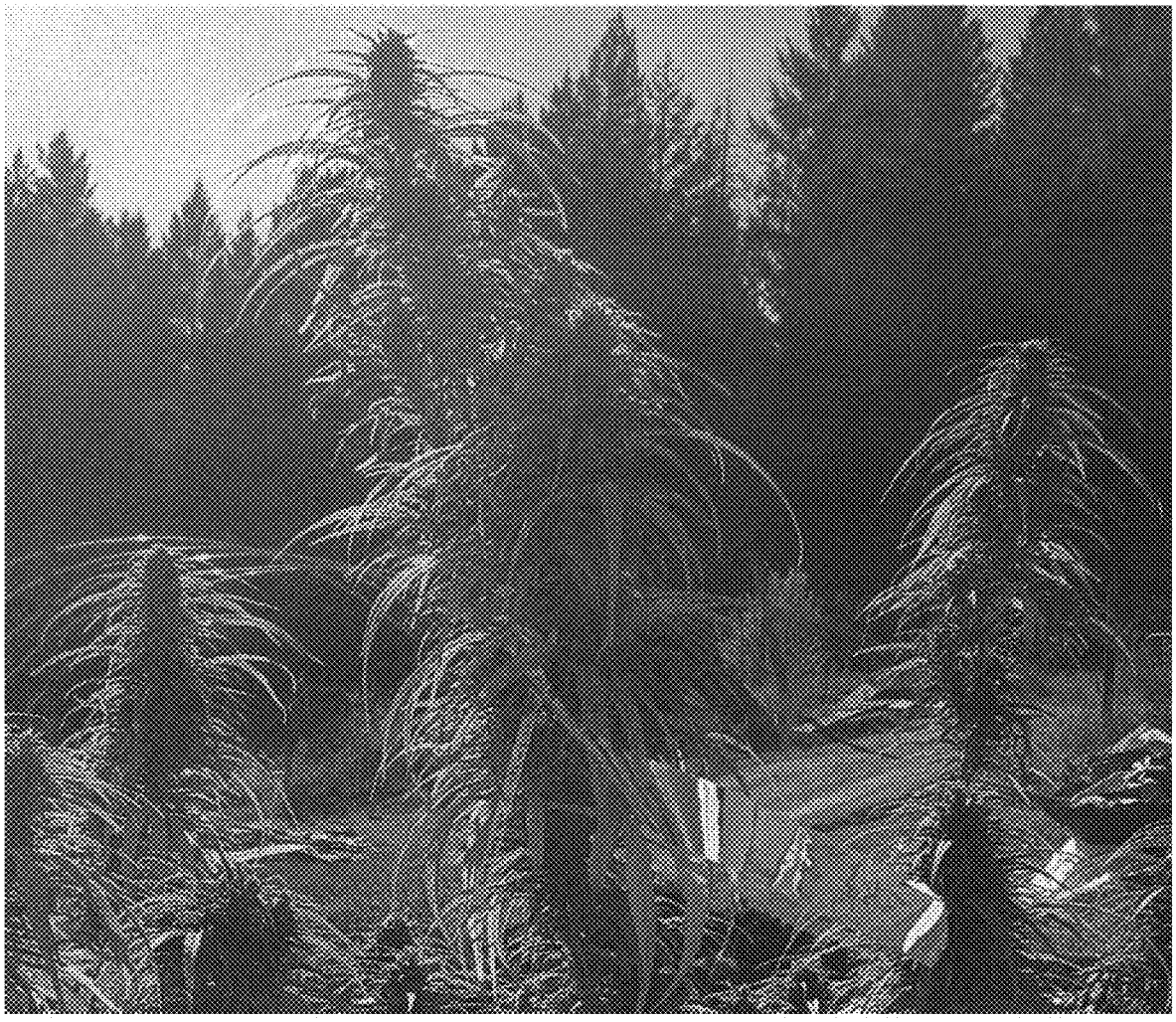
FIG. 5 is a photograph of the inflorescence of the new variety 'V1'.

The following detailed description sets forth the distinctive characteristics of 'V1'. The data which define these characteristics were collected from asexual reproductions of the original selection. Dimensions, sizes, colors, and other characteristics are approximations and averages set forth as accurately as possible. The plant history was taken on plants approximately 3 breeding years of age, and the descriptions relate to plants grown in the field in Laytonville, Calif., U.S.A. Color notations are in reference to the standard digital RGB color-numbering system known to those of ordinary skill in color designation and color matching. Color measurements were taken and quantified using a commercially available color detection, quantification, and matching device. Color group hues and specific color names provided are based upon classification and naming used in the art of color matching and naming, such as can be found at www.color-blindness.com/color-name-hue-tool/color-name-hue.html.

Classification:

a. *Family*.—Cannabaceae.
b. *Genus*.—*Cannabis*.
c. *Species*.—*sativa*.
d. *Common name*.—Marijuana.

Market class: A medicinal herb intended for use as medical oil, and medicinal herb for sale in *Cannabis* dispensaries and for use in the manufacture of medicinal and recreational products.

PLANT

General:

a. *Parentage*.—a. Male parent — M31. b. Female parent — F12.
b. *Growth habit*.—Annual.
c. *Average height*.—2-3 meters.
d. *Average spread*.—2-3 meters.
e. *Growth rate*.—Variable one inch a day.
f. *Branching characteristics*.—Sets of two/matching or alternating.
g. *Length of primary lateral branches*.—1-2 meters.
h. *Quantity of primary lateral branches*.—10-25.
i. *Characteristics of primary branches*.—a. Color — 99866D hue/color group: Brown; color name: Pale Oyster 153,134,109. b. Texture — Sticky, undulated, gritty. c. Strength — Soft to woody.
j. *Cold hardiness*.—Impeded growth under 45° F.
k. *Cold tolerance*.—Survives light snow.
l. *Chilling requirement*.—Flowers below 70° F.
m. *Shipping tolerance*.—High.
n. *Flower storage life*.—One year.
o. *Productivity*.—2-3 lbs in 200 gallon grow bag grown in full sun in Mendocino County.
p. *Disease resistance/susceptibility*.—Powdery Mildew resistant.
q. *Pest resistance/susceptibility*.—Not observed.
r. *Proportion of hermaphrodite plants*.—Low.
s. *Proportion of female plants*.—High.
t. *Proportion of male plants*.—Medium.

STEM

General:

a. *Average diameter*.—2.5 inches plus/minus 1 inch.
b. *Depth of grooves*.—Shallow.
c. *Pith in cross section*.—Thick.
d. *Trichome type*.—Capitate sessile.
e. *Color*.—#7B6847 hue/color group: Yellow; color name: Go Ben 123,104,71.

LEAF

General:

a. *Average length*.—7+/−1 inch.
b. *Average width*.—4.5 inches to 7 inches.
c. *Number of leaflets*.—5-11 depending on plant size and maturity.
d. *Central leaflet length*.—5 inches with a plus/minus of 1 inch grown in 20 gallon pots in a greenhouse.
e. *Central leaflet width*.—0.7 inches with a plus/minus of 0.2 inches.
f. *Margin type*.—Dentate, finely serrated.
g. *Trichome type* (*upper surface*).—Capitate sessile.
h. *Trichome type* (*lower surface*).—Capitate sessile.
i. *Fragrance*.—Herbaceous, vernal, grassy, sweet.

j. *Apex shape*.—Elongated, pointed, thin.
k. *Base shape*.—Palmated.
l. *Quantity*.—High leaf to calyx ratio.
m. *Leaf color* (*top side*).—#2E4626 hue/color group: Green; color name: Palm Leaf 46,70,38.
n. *Leaf color* (*under side*).—#5F6A47 hue/color group: Green; color name: Woodland 95,106,71.
o. *Leaf shape*.—Serrated leaflets with symmetrically variable lengths, palmated.

PETIOLE

General:

a. *Length*.—2 inches plus/minus 0.25 inches.
b. *Surface texture*.—Smooth to gritty depending on maturity.
c. *Anthocyanin intensity*.—Low in Veg state, medium in late flowering stage.
d. *Color*.—#7C613B hue/color group: Brown; color name: Shingle Fawn 124,97,59.

FEMALE FLOWER

General:

a. *Natural flowering season*.—Autumn.
b. *Quantity per inflorescence*.—100-140.
c. *Bracteole*.—i. Shape — Elongated, open cymes. ii. Trichome type — Capitate stalked, glandular. iii. Color — #544D20 hue/color group: Yellow; color name: Bronze Olive 84,77,32.
d. *Stigma*.—i. Size — 0.4 cm. ii. Quantity — 2 per bract. iii. Shape — Acute. iv. Trichome type — Capitate stalked, glandular. v. Color — #585635 hue/color group: Yellow; color name: Thatch Green 88,86,53.
e. *Stipule*.—i. Size — 0.6 cm. ii. Quantity — 2 per pistillate flower. iii. Shape — Pointed, thin, blade-like. iv. Trichome type — Capitate stalked, glandular. v. Color — #4D461C hue/color group: Green; color name: Army Green 77,70,28.
f. *Bract*.—i. Size — 0.1-0.6 cm. ii. Shape — Curved, vaselike, urn shaped. iii. Trichome type — Capitate stalked, glandular. iv. Color — #535736 hue/color group: Green; color name: Waiouru 83,87,54. v. Texture — Sticky, greasy.

COMPARISON BETWEEN PARENTAL AND COMMERCIAL VARIETIES

The new *C. sativa* variety 'V1' differs from the parental varieties, female F12 and male M31, by having an increased production of THCV, is larger in width and height than the F1 stock Ma1 through Ma8, grows more robustly, has much closer internodes, and stronger branches.

Compared to related varieties, 'V1' differs from 'V3' in that 'V3' has coarsely serrated leaflets that are longer than 'V1'. 'V1' is higher in THCV than THC, while 'V3' is higher in THC than THCV. 'V1' finishes later than 'V3', which includes a later flowering cycle and also later development/showing of sex.

'V1' differs from 'V2' primarily with respect to color characteristics of various structures of the two plants, even when grown under the same conditions. Table 2 provides differences in color between 'V1', 'V2' and 'V3' varieties.

TABLE 2

Color comparison between 'V1' and related varieties.

| | 'V1' | 'V2' |
|---|---|---|
| Primary lateral branches | #99866D hue/color group: Brown; color name: Pale Oyster 153,134,109 | #998D71 hue/color group: Brown; color name: Hemp 153,141,113 |
| Stem | #7B6847 hue/color group: Yellow; color name: Go Ben 123,104,71 | #8B7353 hue/color group: Green; color name: Shadow 139,115,83 |
| Top side leaf color | #2E4626 hue/color group: Green; color name: Palm Leaf 46,70,38 | #405A39 hue/color group: Green; color name: Palm Leaf 64,90,57 |
| Under side leaf color | #5F6A47 hue/color group: Green; color name: Woodland 95,106,71 | #718266 hue/color group: Green; color name: Camouflage Green 113,130,102 |
| Petiole | #7C613B hue/color group: Brown; color name: Shingle Fawn 124,97,59 | #A8A65B hue/color group: Green; color name: Green Smoke 168,166,91 |
| Bracteole | #544D20 hue/color group: Yellow; color name: Bronze Olive 84,77,32 | #535B36 hue/color group: Green; color name: Clover 83,91,54 |
| Stigma | #585635 hue/color group: Yellow; color name: Thatch Green 88,86,53 | #5E512D hue/color group: Yellow; color name: West Coast 94,81,45 |
| Stipule | #4D461C hue/color group: Green color name: Army Green 77,70,28 | #7A7A27 hue/color group: Yellow; color name: Pesto 122,122,39 |
| Bract | #535736 hue/color group: Green; color name: Waiouru 83,87,54 | #6E6344 hue/color group: Brown; color name: Tobacco Brown 110,99,68 |

| | 'V3' |
|---|---|
| Primary lateral branches | 8F867E hue/color group: Brown; color name: Schooner 143,134,126 |
| Stem | #726139 hue/color group: Brown; color name: Shingle Fawn 114,97,57 |
| Top side leaf color | #32482A hue/color group: Green; color name: Palm Leaf 50,72,42 |
| Under side leaf color | #586B41 hue/color group: Green; color name: Chalet Green 88,107,65 |
| Petiole | #7FACBE hue/color group: Blue; color name: Glacier 127,172,190 |
| Bracteole | N/A |
| Stigma | #6F5A3C hue/color group: Yellow; color name: Yellow Metal 111,90,60 |
| Stipule | #3A5116 hue/color group: Green; color name: Verdun Green 58,81,22 |
| Bract | #3B5A4E hue/color group: Green; color name: Plantation 59,90,78 |

The new *C. sativa* variety 'V1' differs from variety 'Ecuadorian Sativa' (U.S. Plant Pat. No. 27,475) in several characteristics. 'V1' is narrower in leaf structure than 'Ecuadorian Sativa' Other differences are provided in Table 3:

TABLE 3

| Differences between 'V1' and '*Ecuadorian Sativa*' | | |
|---|---|---|
| | 'V1' | '*Ecuadorian Sativa*' |
| Aroma | Herbaceous,Vernal grassy sweet | Strongly mephitic, with hints of limonene |
| Leaf Margin | finely serrated | coarsely serrated |
| Central leaflets | 5 inches long with a plus/minus of 1 inch | 10-12 cm long |

TABLE 3-continued

| Differences between 'V1' and '*Ecuadorian Sativa*' | | |
|---|---|---|
| | 'V1' | '*Ecuadorian Sativa*' |
| Central leaflet width | 0.7 inches with a plus minus of 0.2 inches | 2.8 cm |
| Petiole | 2 inches with a plus/minus of 0.25 inches | 9-10 cm at maturity |
| Stigma | 0.4 cm | 5-7 mm |

The invention claimed is:

1. A new and distinct variety of *Cannabis* plant named 'V1', substantially as illustrated and described herein.

* * * * *